United States Patent [19]

Fukumaru et al.

[11] 3,961,066
[45] June 1, 1976

[54] 6,7-BENZOMORPHAN DERIVATIVES

[75] Inventors: Toshitsugu Fukumaru, Kyoto; Kenji Kobayashi, Takarazuka; Hiroyuki Mizote, Takarazuka; Shigeho Inaba, Takarazuka; Hisao Yamamoto, Nishinomiya, all of Japan

[73] Assignee: Sumitomo Chemical Company, Limited, Japan

[22] Filed: Mar. 29, 1974

[21] Appl. No.: 456,268

[30] Foreign Application Priority Data

Mar. 31, 1973   Japan.............................. 48-37333

[52] U.S. Cl............................. 424/267; 260/293.54; 260/DIG. 13
[51] Int. Cl.²...................................... C07D 221/26
[58] Field of Search................ 260/293.54, DIG. 13; 424/267

[56] References Cited
UNITED STATES PATENTS

| | | | |
|---|---|---|---|
| 3,639,407 | 2/1972 | Clarke et al. .................. | 260/293.54 |
| 3,700,734 | 10/1972 | Robinson et al. .............. | 260/293.54 |
| 3,793,332 | 2/1974 | Atsumi et al. ................. | 260/293.54 |
| 3,833,595 | 9/1974 | Atsumi et al. ................. | 260/293.54 |

*Primary Examiner*—G. Thomas Todd
*Attorney, Agent, or Firm*—Stewart and Kolasch, Ltd.

[57] ABSTRACT

A novel 2-substituted-6,7-benzomorphan derivative of the formula:

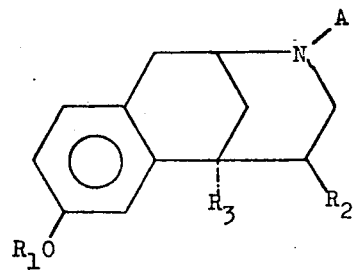

and its acid addition salts, which are useful as non-addicting analgesics and antitussives and can be prepared by reacting a 2-unsubstituted-6,7-benzomorphan derivative of the formula:

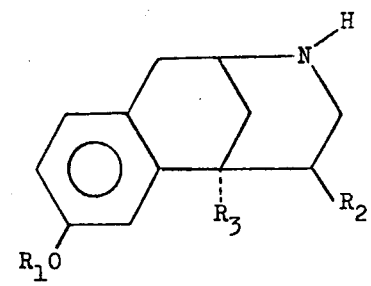

with the reactive derivative of an alcohol of the formula:

HOA', optionally followed by elimination of the protective group in the resulting product, wherein $R_1$ is hydrogen, lower alkyl or acyl; $R_2$ and $R_3$ are each lower alkyl; A is lower alkyl, cyano(lower)alkyl, benzoyl(lower)alkyl, ar(lower)alkyl, lower alkenyl or cyclo(lower)alkyl(lower)alkyl; and A' is a group as mentioned in A or benzoyl(lower)alkyl of which the carbonyl group is masked with a suitable protective group.

16 Claims, No Drawings

6,7-BENZOMORPHAN DERIVATIVES

The present invention relates to novel 6,7-benzomorphan derivatives and their acid addition salts, and their production. More specifically, it relates to novel 2-substituted-4,5-dialkyl-6,7-benzomorphan derivatives of the formula:

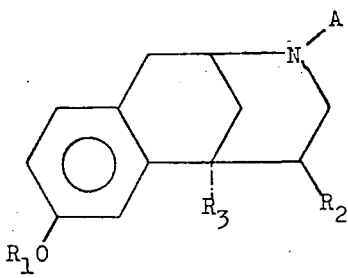

(I)

wherein $R_1$ is a hydrogen atom, a lower alkyl group or an acyl group, $R_2$ and $R_3$ are each a lower alkyl group and A is a lower alkyl group, a cyano(lower)alkyl group, a benzoyl(lower)alkyl group, an ar(lower)alkyl group, a lower alkenyl group or a cyclo(lower)alkyl(-lower)alkyl group and their non-toxic pharmaceutically acceptable acid addition salts, which are useful as analgesics (pain relieving agents) and antitussives, and their production.

In the above significances, the term "lower alkyl" is intended to mean a straight or branched hydrocarbon group having 1 to 5 carbon atoms (e.g. methyl, ethyl, propyl, isopropyl, butyl). The term "acyl" includes $C_2$-$C_6$ alkanoyl (e.g. acetyl, propionyl, butyryl), benzoyl, nicotinoyl, etc. The term "cyano(lower)alkyl" may include cyanoalkyl of which the alkyl moiety has 1 to 3 carbon atoms (e.g. cyanomethyl, β-cyanoethyl, γ-cyanopropyl, γ,γ-dicyanpropyl). The term "benzoyl(lower)alkyl" represents benzoylalkyl of which the alkyl moiety has 1 to 3 carbon atoms and the benzene ring is substituted or not with one or more substituents such as benzoylalkyl, halobenzoylalkyl, alkylbenzoylalkyl (in which the alkyl substituent has 1 to 3 carbon atoms) or alkoxybenzoylalkyl (in which the alkoxy substituent has 1 to 3 carbon atoms). Thus, specific examples of the benzoyl(lower)alkyl group are γ-benzoyl-n-propyl, β-benzoylethyl, γ-(p-methoxybenzoyl)-n-propyl, γ-(p-fluorobenzoyl)-n-propyl, γ-(o,p-difluorobenzoyl)-n-propyl, β-(p-fluorobenzoyl)-ethyl, γ-(p-chlorobenzoyl)-n-propyl, etc. The term "ar(-lower)-alkyl" indicates phenylalkyl of which the alkyl moiety has 1 to 3 carbon atoms and the benzene ring is substituted or not with one or more substituents such as phenylalkyl (e.g. benzyl, phenethyl), alkylphenylalkyl (in which the alkyl substituent has 1 to 3 carbon atoms) (e.g. p-methylphenethyl) or nitrophenylalkyl (e.g. p-nitrophenethyl). The term "lower alkenyl" includes $C_3$-$C_7$ alkenyl (e.g. allyl, γ-methyl-β-butenyl, methylallyl). The term "cyclo(lower)alkyl(lower)alkyl" may represent a cycloalkylalkyl group of which the cycloalkyl moiety has 3 to 7 carbon atoms and the alkyl moiety has 1 to 3 carbon atoms. Further, it may bear $C_1$-$C_3$ alkyl on the cycloalkane ring. Thus, specific examples of the cycloalkylalkyl group are cyclopropylmethyl, cyclobutylmethyl, methylcyclobutylmethyl, cyclopentylmethyl, etc.

Hitherto, many benzomorphan derivatives have been developed as potent analgesics, but most of them have addiction liability and/or other unfavorable side actions.

As the result of the study seeking 6,7-benzomorphan derivatives which have a potent analgesic activity and do not show any drug dependency in human beings and animals, it has now been found that the 6,7-benzomorphan derivatives (I) have a potent analgesic activity with a calmative effect and do not show any drug dependency and are useful as analgesics and antitussives.

Accordingly, a main object of the present invention is to provide the 6,7-benzomorphan derivatives (I) and their non-toxic pharmaceutically acceptable salts. Another object of this invention is to provide a process for production of the 6,7-benzomorphan derivatives (I). A further object of the invention is to provide a composition comprising at least one of the 6,7-benzomorphan derivatives (I) and their non-toxic pharmaceutically acceptable salts. These and other objects of the invention will be apparent to those skilled in the art from the foregoing and following descriptions.

Among the 6,7-benzomorphan derivatives (I), a preferred group of compounds is representable by the formula:

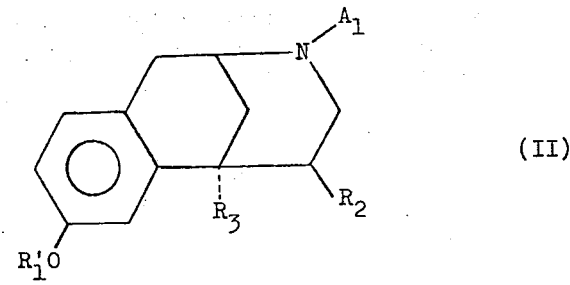

(II)

wherein $R_2$ and $R_3$ are each as defined above, $R'_1$ is a hydrogen atom, a methyl group or an acetyl group and $A_1$ is a lower alkyl group, a cyano(lower)alkyl group, a benzoyl(lower)alkyl group, an ar(lower)alkyl group or a lower alkenyl group.

A more preferred group of compounds is representable by the formula:

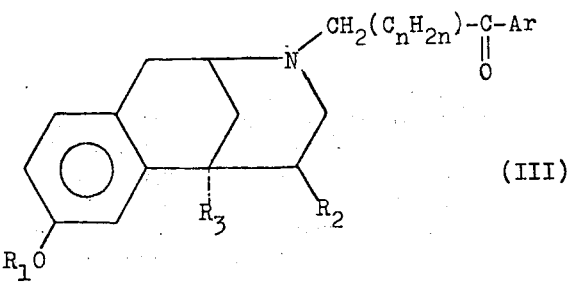

(III)

wherein $R_1$, $R_2$ and $R_3$ are each as defined above, Ar is a phenyl group, a halophenyl group or a lower alkoxyphenyl group and n is an integer of 1 or 2. In the compounds (III), particularly preferred are those of the formula (III) wherein $R_1$ is a hydrogen atom, a methyl group or an acetyl group and $R_2$, $R_3$, Ar and n are each as defined above. More particularly preferred are those of the formula (III) wherein $R_1$ is a hydrogen atom, a methyl group or an acetyl group, n is an integer of 2 and $R_2$, $R_3$ and Ar are each as defined above.

The most preferred compounds are represented by the formula:

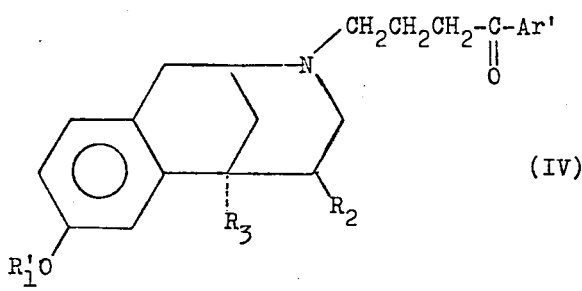

wherein $R_2$ and $R_3$ are each a methyl group, Ar' is a phenyl group substituted or not with one or more fluorine atoms and/or methoxy groups and $R'_1$ is as defined above.

According to the present invention, the objective 6,7-benzomorphan derivative (I), i.e. the one having a substituent at the 2-position, can be produced by reacting the corresponding 2-unsubstituted-6,7-benzomorphan derivative of the formula:

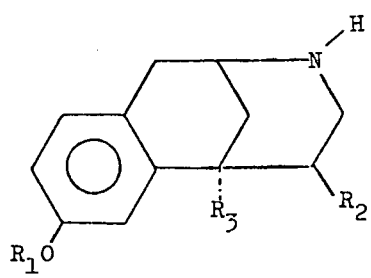

wherein $R_1$, $R_2$ and $R_3$ are each as defined above with a reactive derivative of an alcohol of the formula:

HOA'  (VI)

wherein A' is a lower alkyl group, a cyano(lower)alkyl group, a benzoyl(lower)alkyl group, an ar(lower)alkyl group, a lower alkenyl group, a cyclo(lower)alkyl(lower)alkyl group or a benzoyl(lower)alkyl group of which the carbonyl group is masked with a suitable protective group (e.g. ethylenedioxy, ethylenedithio, propylenedioxy) and, if desired, eliminating the protective group from the reaction product.

The reactive derivative of the alcohol (VI) may be the one corresponding to the alcohol (VI) by the hydroxyl group being replaced by an alkylsulfonyloxy group (e.g. methylsulfonyloxy), an arylsulfonyloxy group (e.g. tosyloxy) or a halogen atom (e.g. chlorine, bromine, iodine).

The reaction is usually carried out in an inert solvent (e.g. n-hexane, benzene, toluene, xylene, chloroform, dimethylformamide, methanol, ethanol, isopropanol). In the reaction, the presence of a base (e.g. sodium carbonate, potassium carbonate, sodium bicarbonate, potassium hydroxide, potassium t-butoxide, sodium methoxide, phenyl lithium, sodium amide, sodium hydride, pyridine, triethylamine) is generally preferred. The reaction proceeds at a temperature of 20° to 200°C, preferably 50° to 170°C. The reaction product is readily isolated from the reaction mixture by a conventional separation procedure.

The subsequent elimination of the protective group, which may be optionally carried out, can be accomplished by hydrolysis, for instance, with an acid (e.g. hydrochloric acid).

The 6,7-benzomorphan derivative (I) wherein $R_1$ is an acyl group may be produced by acylating the corresponding 6,7-benzomorphan derivative (I) wherein $R_1$ is a hydrogen atom in a per se conventional procedure, e.g. treating with an acid anhydride or an acid halide such as an acid chloride or an acid bromide.

The 6,7-benzomorphan derivative (I) wherein $R_1$ is an alkyl group may be prepared by alkylating the corresponding 6,7-benzomorphan derivative (I) wherein $R_1$ is a hydrogen atom in a per se conventional procedure, e.g. treating with an alkylating agent such as diazomethane, dimethyl sulfate or an alkyl halide (e.g. methyl chloride, ethyl bromide, ethyl iodide).

For the preparation of the optically active isomer of the 6,7-benzomorphan derivative (I), the corresponding racemate may be resolved by a conventional optical resolution method.

The 6,7-benzomorphan derivative of the formula:

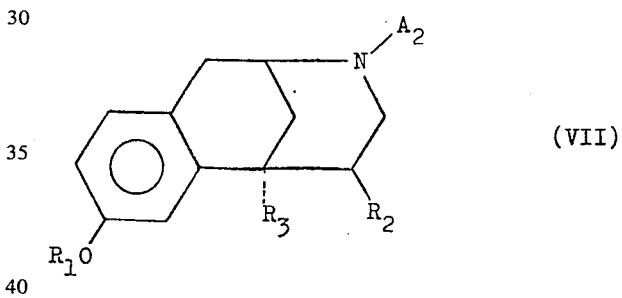

wherein $R_1$, $R_2$ and $R_3$ are each as defined above and $A_2$ is a lower alkyl group, a benzoyl(lower)alkyl group, an ar(lower)alkyl group or a cyclo(lower)alkyl(lower)alkyl group may be prepared by cyclizing a tetrahydropyridine derivative of the formula:

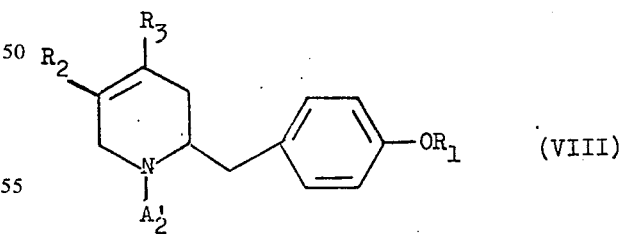

wherein $R_1$, $R_2$ and $R_3$ are each as defined above and $A'_2$ is a lower alkyl group, a benzoyl(lower)alkyl group, an ar(lower)-alkyl group, a cyclo(lower)alkyl(lower)alkyl group or a benzoyl(lower)alkyl group of which the carbonyl group is masked with a suitable protective group. The cyclization may be accomplished by treatment with a mineral acid (e.g. hydrobromic acid, hydrochloric acid, phosphoric acid) or a Lewis acid (e.g. aluminum bromide, aluminum chloride, boron trifluoride). In case of using the mineral acid, the cyclization may be carried out in the mineral acid itself as a solvent, and the reaction proceeds at an elevated temperature. In case of using the Lewis acid, the reaction may be performed in an inert solvent (e.g. carbon disulfide, tetrachloroethane) which is known as a solvent for the Friedel-Crafts reaction, and the intramolecular alkylation proceeds at room temperature.

The 6,7-benzomorphan derivative of the formula:

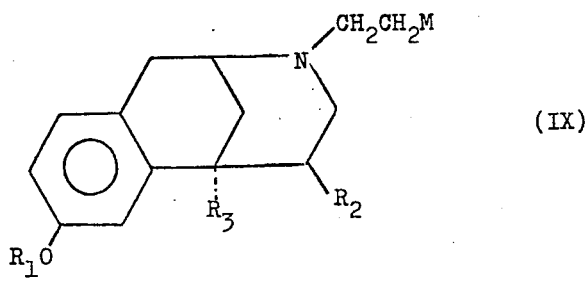

(IX)

wherein M is a benzoyl group or a cyano group and $R_1$, $R_2$ and $R_3$ are each as defined above may be produced by reacting the 2-unsubstituted 6,7-benzomorphan derivative (V) with a compound of the formula:

(X)

wherein M is as defined above. The reaction is the so-called Michael type addition, which can easily proceed at room temperature in an inert solvent (e.g. methanol, ethanol, dimethylformamide, tetrahydrofuran) or in an excess of the compound (X) as a solvent.

The 6,7-benzomorphan derivative (III) wherein n is an integer of 2 can be produced by Hofmann degradation of a quaternary ammonium compound of the formula:

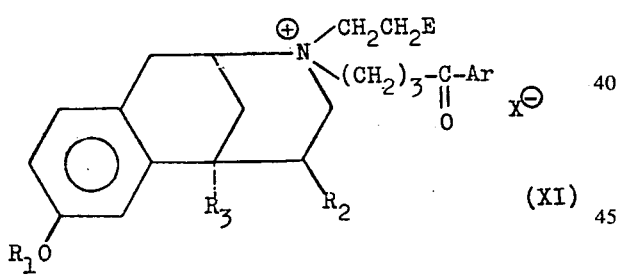

(XI)

wherein $R_1$, $R_2$, $R_3$ and Ar are each as defined above, E is an aryl group, a cyano group, a nitro group, an acyl group, a carbalkoxy group or a carboxyl group and X is a halogen atom. The reaction readily proceeds by treatment with a strong base (e.g. potassium hydroxide, sodium hydroxide, potassium t-butoxide, sodium methoxide) or by heating at an elevated temperature.

The 6,7-benzomorphan derivative (III) can be also produced by reductively eliminating an arylmethyl group from a quaternary ammonium compound of the formula:

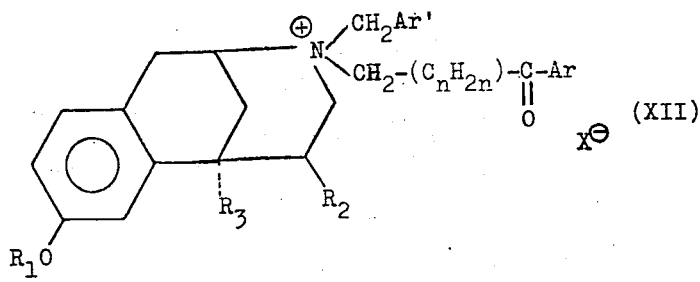

(XII)

wherein $R_1$, $R_2$, $R_3$, Ar, n and X are each as defined above and Ar' is an aryl group. The reductive elimination may be accomplished by hydrogenating the quaternary ammonium compound (XII) in a polar solvent (e.g. methanol, ethanol, dimethylformamide) in the presence of a catalyst (e.g. Raney nickel, platinum black, palladium carbon) until equimolar hydrogen absorption is ceased.

The 6,7-benzomorphan derivative (III) can be further produced by acylating the 2-unsubstituted-6,7-benzomorphan derivative (V) with a reactive derivative of a carboxylic acid of the formula:

(XIII)

wherein Ar and n are each as defined above and Y is a halogen atom, a lower alkoxycarbonyloxy group or an aryloxycarbonyloxy group, reducing the resulting compound of the formula:

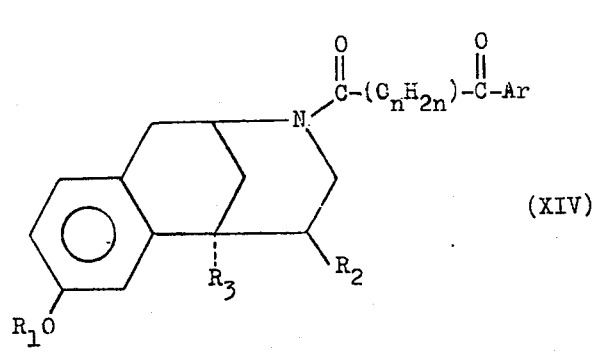

(XIV)

wherein $R_1$, $R_2$, $R_3$, Ar and n are each as defined above with a reducing agent (e.g. lithium aluminum hydride, diborane) and oxidizing the resultant compound of the formula:

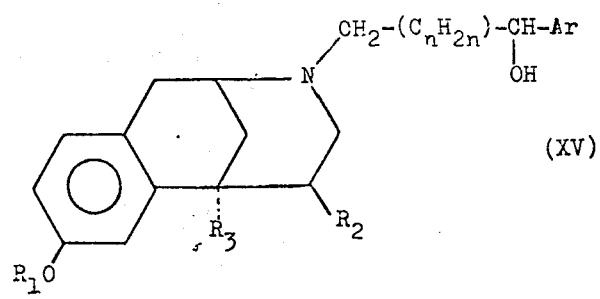

(XV)

wherein $R_1$, $R_2$, $R_3$, Ar and n are each as defined above with an oxidizing agent (e.g. chromium trioxide, manganese dioxide).

The starting compounds (V) and (VIII) are new compounds, which may be analogously produced by the method described in Journal of Medicinal Chemistry, 14, 565 (1971). The compound (VIII) may be also produced by the method as shown in the following formulae:

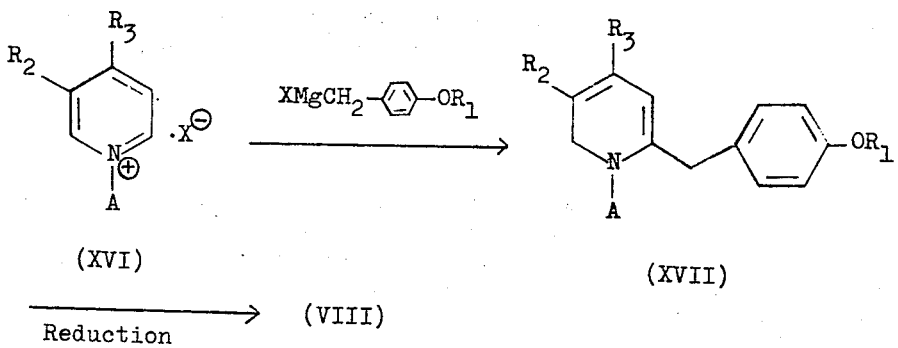

(VIII)

wherein $R_1$, $R_2$, $R_3$, A and X are each as defined above. The produced compound (VIII) can be separated from its isomer and purified by a conventional procedure such as fractional distillation or fractional recrystallization.

Various acid addition salts of the 6,7-benzomorphan derivative (I) can be obtained by the use of organic and inorganic acids such as formic acid, acetic acid, propionic acid, butyric acid, malic acid, fumaric acid, succinic acid, glutamic acid, tartaric acid, oxalic acid, citric acid, lactic acid, maleic acid, hydroxymaleic acid, glycolic acid, gluconic acid, glucuronic acid, saccharic acid, ascorbic acid, phenylacetic acid, benzoic acid, p-aminobenzoic acid, phthalic acid, salicylic acid, anthranilic acid, p-hydroxybenzoic acid, p-aminosalicylic acid, picolinic acid, 3-hydroxy-2-naphthoic acid, 3-indoleacetic acid, barbituric acid, sulfamic acid, quininic acid, tropic acid, methanesulfonic acid, ethanesulfonic acid, benzenesulfonic acid, p-toluenesulfonic acid, hydroxyethanesulfonic acid, hydrofluoric acid, hydrochloric acid, hydrobromic acid, hydroiodic acid, perchloric acid, nitric acid, sulfuric acid, phosphoric acid and the like.

Specific examples of the 6,7-benzomorphan derivative (I) obtained by the present invention are as follows:

2′-Hydroxy-2-[γ-(p-fluorobenzoyl)-n-propyl]-4,5-dimethyl-6,7-benzomorphan;

2′-Hydroxy-2-[γ-(o,p-difluorobenzoyl)-n-propyl]-4,5-dimethyl-6,7-benzomorphan;

2′-Hydroxy-2-[γ-(p-methoxybenzoyl)-n-propyl]-4,5-dimethyl-6,7-benzomorphan;

2′-Hydroxy-2-(γ-benzoyl-n-propyl)-4,5-dimethyl-6,7-benzomorphan;

2′-Hydroxy-2-[β-(p-fluorobenzoyl)ethyl]-4,5-dimethyl-6,7-benzomorphan;

2′-Acetoxy-2-[γ-(p-fluorobenzoyl)-n-propyl]-4,5-dimethyl-6,7-benzomorphan;

2′-Methoxy-2-[γ-(p-fluorobenzoyl)-n-propyl]-4,5-dimethyl-6,7-benzomorphan;

2′-Hydroxy-2,4,5-trimethyl-4,5-dimethyl-6,7-benzomorphan;

2′-Hydroxy-2-(β-cyanoethyl)-4,5-dimethyl-6,7-benzomorphan;

2′-Hydroxy-2-(γ-cyanopropyl)-4,5-dimethyl-6,7-benzomorphan;

2′-Hydroxy-2-(β-phenylethyl)-4,5-dimethyl-6,7-benzomorphan;

2′-Hydroxy-2-(γ-methyl-β-butenyl)-4,5-dimethyl-6,7-benzomorphan;

2′-Hydroxy-2-cyclopropylmethyl-4,5-dimethyl-6,7-benzomorphan, etc.

The 6,7-benzomorphan derivatives (I) and their salts have a strong analgesic activity but do not show any addiction liability.

When, for example, 2′-hydroxy-2-[γ-(p-fluorobenzoyl)-n-propyl]-4,5-dimethyl-6,7-benzomorphan was administered subcutaneously to rats everyday for 4 weeks, the animals did not produce any physical dependency as shown in Table 1.

Table 1

| Compound | Dose mg/kg/day for 4 weeks | Abstinence syndrome |
| --- | --- | --- |
| 2′-Hydroxy-2-[γ-(p-fluorobenzoyl)-n-propyl-4,5-dimethyl-6,7-benzomorphan | 40 | — |
| Morphine.HCl | 20 | +++ |

Note: Groups of animals of male rats of Wistar strain (body weight, 150 g), each group consisting of 20 male rats, were subcutaneously given the test compound twice a day for 4 consecutive weeks. On the next day after drug withdrawal, the body weight was measured. The symbols have the following meanings: +++, severe decrease (about 5 % decrease); ++, moderate decrease; +, mild decrease; —, no decrease. The marked decrease is taken as an indication of the possession of a narcotic property by the test compound.

Further, for example, 2′-hydroxy-2-[γ-(p-fluorobenzoyl)-n-propyl]-4,5-dimethyl-6,7-benzomorphan and 2′-hydroxy-2-(β-phenylethyl)-4,5-dimethyl-6,7-benzomorphan exhibited a more potent analgesic activity than morphine and a much more potent analgesic activity than pentazocin (i.e. 2′-hydroxy-2-γ-methyl-β-butenyl-5,9-dimethyl-6,7-benzomorphan), the latter being one of the strongest commercial analgesics, as shown in Table 2.

Table 2

| Compound | ED$_{50}$ (mg/kg) |
| --- | --- |
| 2'-Hydroxy-2-[γ-(p-fluorobenzoyl)-n-propyl]-4,5-dimethyl-6,7-benzomorphan | 0.36 |
| 2'-Hydroxy-2-(β-phenylethyl)-4,5-dimethyl-6,7-benzomorphan | 0.23 |
| Pentazocin | 17.5 |
| Morphine | 1.2 |

Note: The test was based on the specific antagonism of the test compound to the typical syndrome produced by intraperitoneal injection of 0.6 % aqueous acetic acid. The syndrome was characterized by intermittent contractions of the abdomen, twisting and turning of the trunk and extension of the hind legs. A group of 5 mice was used for each dose level. The test compound was administered subcutaneously 20 minutes before the injection of acetic acid. The number of mice which showed no pain response was recorded. The ED$_{50}$ value was calculated according to the Litchfield-Wilcoxon's method.

Accordingly, the 6,7-benzomorphan derivatives (I) and their salts may be formulated in pharmaceutical preparations with pharmaceutically acceptable carriers or diluents. For example, the 6,7-benzomorphan derivatives (I) can be prepared for use by dissolving under sterile conditions a salt form of them in water (or an equivalent or greater amount of a pharmaceutically acceptable acid if the free base is used instead of the salt), or in a physiologically compatible aqueous medium such as saline, and stored in ampoules for use by injection. For injection the compounds of this invention are administered subcutaneously or intramuscularly in the range of about 1 mg to about 200 mg per day. Alternatively, they can be incorporated in a unit dosage (1 – 15 mg) form as tablets or capsules for oral administration either alone or in combination with suitable adjuvants such as lactose, starch, calcium carbonate, talc, magnesium stearate and gum acacia.

Practical and presently preferred embodiments of the present invention are shown in the following Examples.

EXAMPLE 1

A mixture of 1.09 g of 2'-hydroxy-4,5-dimethyl-6,7-benzomorphan, 1.10 g of 1,1-ethylenedioxy-1-(p-fluorophenyl)-4-chlorobutane, 0.63 g of anhydrous sodium bicarbonate and 15 ml of anhydrous dimethylformamide was refluxed for 4 hours. Removal of the solvent under reduced pressure, dilution with 20 ml of water, extraction with 20 ml of chloroform, drying over anhydrous sodium sulfate, filtration and evaporation of the solvet afforded a brown oily residue. The residue was dissolved in a mixture of 10 ml of methanol, 5.2 ml of water and 1.2 ml of concentrated hydrochloric acid. The solution was refluxed for 1 hour, diluted with water, basified with concentrated aqueous ammonia and extracted with chloroform. The extract was washed, dried and evaporated to dryness to give a brown solid, which was purified by column chromatography over silicic acid to afford 2'-hydroxy-2-[γ-(p-fluorobenzoyl)-n-propyl]-4,5-dimethyl-6,7-benzomorphan as an amorphous white solid. M.P. 95.0° – 105.0°C.

In the same manner as above, there were prepared the following compounds: 2'-hydroxy-2-[γ-(o,p-difluorobenzoyl)-n-propyl]-4,5-dimethyl-6,7-benzomorphan, M.P. 139.0° – 143.0°C; 2'-hydroxy-2-(γ-benzoyl-n-propyl)-4,5-dimethyl-6,7-benzomorphan, M.P. 60.0° – 65.0°C; 2'-hydroxy-2-[γ-(p-methoxybenzoyl)-n-propyl]-4,5-dimethyl-6,7-benzomorphan, n$_D^{25}$ = 1.5550; 2'-hydroxy-2-[β-(p-fluorobenzoyl)ethyl]-4,5-dimethyl-6,7-benzomorphan, M.P. 185.0° – 193.0°C (decomp.), etc.

EXAMPLE 2

A solution of 0.5 g of 2'-hydroxy-2-[γ-(p-fluorobenzoyl)-n-propyl]-4,5-dimethyl-6,7-benzomorphan in 10 ml of acetic anhydride was heated at 100°C for 1 hour. Evaporation of the excess acetic anhydride under reduced pressure, neutralization with sodium carbonate, extraction with ether, washing with water, drying and evaporation of the solvent gave 2'-acetoxy-2-[γ-(p-fluorobenzoyl)-n-propyl]-4,5-dimethyl-6,7-benzomorphan. n$_D^{23}$ = 1.5539.

EXAMPLE 3

To a solution of 0.5 g of 2'-hydroxy-2-[γ-(p-fluorobenzoyl)-n-propyl]-4,5-dimethyl-6,7-benzomorphan in 20 ml methanol, there were added 30 ml of an ether solution of diazomethane, and the reaction mixture was stirred at room temperature for 20 hours. Evaporation of the excess diazomethane and the solvent afforded an oily residue which was chromatographed on silicic acid to give 2'-methoxy-2-[γ-(p-fluorobenzoyl)-n-propyl]-4,5-dimethyl-6,7-benzomorphan. n$_D^{25}$ = 1.5625.

EXAMPLE 4

A mixture of 1.09 g of Z'-hydroxy-4,5-dimethyl-6,7-benzomorphan, 1.02 g of β-phenylethyl chloride, 0.63 g of sodium bicarbonate and 15 ml of anhydrous dimethylformamide was refluxed for 4 hours. Removal of the solvent, dilution with water, extraction with chloroform, drying, evaporation and crystallization with ether gave a crystalline product, which was recrystallized from ethyl acetate to give 0.5 g of 2'-hydroxy-2-(β-phenylethyl)-4,5-dimethyl-6,7-benzomorphan. M.P. 151.0°C.

In the same manner as above, there were prepared the following compounds: 2'-hydroxy-2,4,5-trimethyl-6,7-benzomorphan, M.P. 207.0°C; 2'-hydroxy-2-(γ-cyano-n-propyl)-4,5-dimethyl-6,7-benzomorphan, M.P. 163.5°C; 2'-hydroxy-2-(β-cyanoethyl)-4,5-dimethyl-6,7-benzomorphan, M.P. 129.0°C; 2'-hydroxy-2-cyclopropylmethyl-4,5-dimethyl-6,7-benzomorphan, M.P. 187.0°C; 2'-hydroxy-2-(γ-methyl-β-butenyl)-4,5-dimethyl-6,7-benzomorphan, M.P. 183.0°C, etc.

EXAMPLE 5 p-Anisyl chloride (775 g) was reacted with magnesium (469 g) in anhydrous ether (3600 g) to give an ether solution of p-anisylmagnesium chloride. This solution was added dropwise to a suspension of 1,3,4-trimethylpyridinium iodide (822 g) in anhydrous ether (1157 g) while stirring, and stirring was continued at room temperature for 7 hours. The reaction mixture was poured into a solution of ammonium chloride (541 g) in water (541 g) and stirred for a while. The ether layer was separated and shaken with 10 % hydrochloric acid (2700 g). The acidic layer was made alkaline with 28 % aqueous ammonia and extracted with ether (3000 g). The ether layer was washed with a saturated aqueous solution of sodium chloride (3000 g), dried over anhydrous sodium sulfate (270 g), filtered and concentrated. The concentrate was dissolved in a mixture of methanol (859 g) and 1N sodium hydroxide solution (1084 g), sodium borohydride (81 g) was added thereto and the resulting mixture was stirred at 55° to 60°C for 2 hours. To the reaction mixture, water (3620 g) was added, and the resulting mixture was extracted with ether (2070 g). The extract was dried over anhydrous sodium sulfate (181 g) and filtered. The filtrate was concentrated to give a mixture of 2-(p-methoxybenzyl)-1,4,5-trimethyl-2,3,3,6-tetrahydropyridine and 2-(p-methoxybenzyl)-1,3,4-trimethyl-2,3,3,6-tetrahydropyridine in a proportion of 49 : 29 by weight (determined by gas chromatographic analysis).

Distillation of the mixture (100 g) afforded 2-(p-methoxybenzyl)-1,3,4-trimethyl-2,3,3,6-tetrahydropyridine as a fraction boiling at 128° to 130°C/0.7 mmHg and 2-(p-methoxybenzyl)-1,4,5-trimethyl-2,3,3,6-tetrahydropyridine (21 g) as a fraction boiling at 135° to 140°C/0.7 mmHg. In addition, the mixture (245 g) was reacted with oxalic acid (90 g) in methanol. The resulting oxalate was recrystallized twice from a mixture of acetone and methanol, treated with ammonia alkali, extracted with ether and concentrated to give 2-(p-methoxybenzyl)-1,4,5-trimethyl-2,3,3,6-tetrahydropyridine (82 g).

A solution of 123 g of 2-(p-methoxbenzyl)-1,4,5-trimethyl-2,3,3,6-tetrahydropyridine in 914 g of 47 % hydrobromic acid was refluxed for 22 hours. Basification with concentrated aqeuous ammonia, extraction with chloroform, evaporation of the solvent and trituration with acetone afforded crude crystals, which were recrystallized from methanol to give 48 g of 2'-hydroxy-2,4,5-trimethyl-6,7-benzomorphan. M.P. 207.0°C.

In the same manner as above, there were prepared the following compounds: 2'-hydroxy-2-(β-phenylethyl)-4,5-dimethyl-6,7-benzomorphan, M.P. 151.0°C; 2'-hydroxy-2-[γ-(p-fluorobenzoyl)-n-propyl]-4,5-dimethyl-6,7-benzomorphan, M.P. 93.0° – 102.0°C, etc.

EXAMPLE 6

To a solution of 1.1 g of 2'-hydroxy-4,5-dimethyl-6,7-benzomorphan in 30 ml of methanol, there was added 1.0 g of acrylonitrile, and the mixture was refluxed for 1 hour. Evaporation of the excess acrylonitrile and the solvent, and trituration with acetone gave crude crystals, which were recrystallized from methanol to give z'-hydroxy-2-(β-cyanoethyl)-4,5-dimethyl-6,7-benzomorphan, M.P. 129.0°C.

In the same manner as above, there was prepared 2'-hydroxy-2-[β-(p-fluorobenzoyl)ethyl]-4,5-dimethyl-6,7-benzomorphan, M.P. 185.0° – 193.0°C (decomp.).

EXAMPLE 7

To a solution of 1.0 g of potassium in 30 ml of t-butanol, there were added 3.0 g of 2'-hydroxy-2-β-phenethyl-2-[γ-(p-fluorobenzoyl)-n-propyl]-4,5-dimethyl-6,7-benzomorphanium bromide, and the mixture was refluxed for 10 minutes. Dilution with water, extraction with chloroform, washing with water, drying and evaporation of the solvent afforded an amorphous residue, which was chromatographed on silicic acid to give 2'-hydroxy-[γ-(p-fluorobenzoyl)-n-propyl-4,5-dimethyl-6,7-benzomorphan, M.P. 93.5° – 104.5°C.

EXAMPLE 8

To a solution of 1.96 g of β-(p-fluorobenzoyl)-propionic acid in 40 ml of chloroform, there were added 1.01 g of triethylamine and 1.09 g of ethyl chloroformate at 0°C. The resulting mixture was stirred for 30 minutes, 2'-hydroxy-4,5-dimethyl-6,7-benzomorphan was added thereto and stirring was continued overnight. Dilution with chloroform, washing with dilute hydrochloric acid, aqueous sodium bicarbonate and water successively, drying and evaporation of the solvent afforded 2'-[β-(p-fluorobenzoyl)propionyloxy]-2-[β-(p-fluorobenzoyl)propionyl]-4,5-dimethyl-6,7-benzomorphan. This product was added to a suspension of 1 g of lithium aluminum hydride in 40 ml of anhydrous tetrahydrofuran. The reaction mixture was refluxed under stirring for 6 hours. Decomposition of the excess lithium aluminium hydride with water, filtration with celite, dilution with water, extraction with chloroform, drying and evaporation of the solvent afforded 2'-hydroxy-2-[δ-(p-fluorophenyl)-δ-hydroxy-n-butyl]-4,5-dimethyl-6,7-benzomorphan. This compound was dissolved in 20 ml of acetone, and 8N Jones reagent (a mixture of chromium trioxide, concentrated sulfuric acid and water) was dropwise added thereto at −5°C to 0°C until the red color of the Jones reagent did not vanish so rapidly. Dilution with ice water, basification with aqueous ammonia, extraction with chloroform, washing and evaporation of the solvent gave crude 2'-hydroxy-2-[γ-(p-fluorobenzoyl)-n-propyl]-4,5-dimethyl-6,7-benzomorphan, which was chromatographed on silicic acid. M.P. 92.0° – 104.0°C.

Preparation of 2'-hydroxy-4,5-dimethyl-6,7-benzomorphan

A mixture of 2'-hydroxy-2,4,5-trimethyl-6,7-benzomorphan (15 g) and acetic anhydride (35 g) was refluxed for 1 hour. After removal of acetic anhydride, the reaction mixture was dissolved into benzene, washed with sodium carbonate and water, dried over anhydrous sodium sulfate, filtered and concentrated. A mixture of the thus obtained acetyl compound, cyanogen bromide (14 g) and chloroform (60 ml) was refluxed for 3 hours and then chloroform was distilled away. To the mixture, 6 % hydrochloric acid (170 ml) was added, and refluxing was effected for 12 hours. The reaction mixture was made alkaline with ammonia, extracted with a mixture of butanol and benzene, dried, filtered and concentrated. The concentrate was crystallized with acetone and recrystallized from methanol to give 2'-hydroxy-4,5-dimethyl-6,7-benzomorphan (6.5 g). M.P. 221.6°C.

What is claimed is:

1. A 6,7-benzomorphan of the formula:

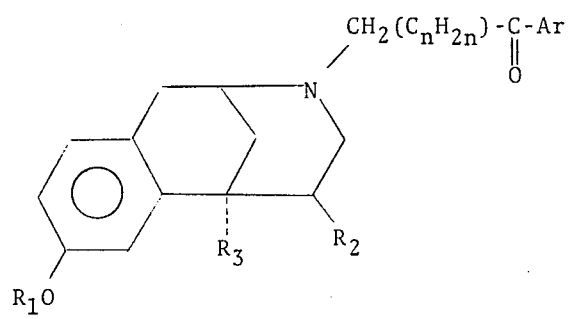

and non-toxic, pharmaceutically acceptable acid addition salts thereof, wherein $R_1$ is a hydrogen atom, a lower alkyl group, $C_2$-$C_6$ alkanoyl, benzoyl or nicotinoyl, $R_2$ and $R_3$ are each a lower alkyl group, Ar is a phenyl group, a halophenyl group or a lower alkoxyphenyl group and n is an integer of 1 or 2.

2. The 6,7-benzomorphan derivative according to claim 1, wherein $R_1$ is a hydrogen atom, a methyl group or an acetyl group, and non-toxic, pharmaceutically acceptable acid addition salts thereof.

3. The 6,7-benzomorphan derivative according to claim 2, wherein n is the integer 2, and non-toxic, pharmaceutically acceptable acid addition salts thereof.

4. 2'-Hydroxy-2-[γ-(p-fluorobenzoyl)-n-propyl]-4,5-dimethyl-6,7-benzomorphan.

5. 2'-Acetoxy-2-[γ-(p-fluorobenzoyl)-n-propyl]-4,5-dimethyl-6,7-benzomorphan.

6. 2'-Methoxy-2-[γ-(p-fluorobenzoyl)-n-propyl]-4,5-dimethyl-6,7-benzomorphan.

7. 2'-Hydroxy-2-[γ-(o,p-difluorobenzoyl)-n-propyl]-4,5-dimethyl-6,7-benzomorphan.

8. 2'-Hydroxy-2-(γ-benzoyl-n-propyl)-4,5-dimethyl-6,7-benzomorphan.

9. 2'-Hydroxy-2-[γ-(p-methoxybenzoyl)-n-propyl]-4,5-dimethyl-6,7-benzomorphan.

10. 2'-Hydroxy-2-[β-(p-fluorobenzoyl)ethyl]-4,5-dimethyl-6,7-benzomorphan.

11. A pharmaceutical composition comprising an analgesically effective amount of the 6,7-benzomorphan derivative according to claim 1 as an active ingredient and a pharmaceutically acceptable carrier or diluent.

12. A pharmaceutical composition according to claim 11, wherein said composition is in the form of a tablet.

13. A pharmaceutical composition according to claim 11, wherein said composition is in the form of a capsule.

14. A pharmaceutical composition according to claim 11, wherein said composition is in the form of an injectable solution.

15. A method for the use of the 6,7-benzomorphan derivative according to claim 1 as an analgesic or antitussive agent which comprises administering an effective analgesic or antitussive amount of said derivative to an animal or human being.

16. The method of claim 15, wherein said derivative is incorporated with a pharmaceutically acceptable carrier or diluent.

* * * * *